(12) United States Patent
Jaaskelainen

(10) Patent No.: US 9,074,988 B2
(45) Date of Patent: Jul. 7, 2015

(54) FIBER OPTIC SENSING SYSTEM WITH HYDROGEN FLUSH

(71) Applicant: Halliburton Energy Services, Inc, Houston, TX (US)

(72) Inventor: Mikko Jaaskelainen, Katy, TX (US)

(73) Assignee: Halliburton Energy Services, Inc, Houston, TX (US)

( * ) Notice: Subject to any disclaimer, the term of this patent is extended or adjusted under 35 U.S.C. 154(b) by 190 days.

(21) Appl. No.: 13/910,635

(22) Filed: Jun. 5, 2013

(65) Prior Publication Data

US 2014/0363117 A1  Dec. 11, 2014

(51) Int. Cl.
  *G02B 6/00* (2006.01)
  *G01N 21/15* (2006.01)
  *G02B 6/44* (2006.01)
  *E21B 17/20* (2006.01)

(52) U.S. Cl.
  CPC .............. *G01N 21/15* (2013.01); *E21B 17/206* (2013.01); *G02B 6/4415* (2013.01)

(58) Field of Classification Search
  CPC ....... E21B 17/206; E21B 47/125; G02B 6/00; G02B 6/4415
  USPC ..................................................... 385/12–13
  See application file for complete search history.

(56) References Cited

U.S. PATENT DOCUMENTS

| | | | |
|---|---|---|---|
| 6,907,170 B1 | 6/2005 | Maida, Jr. | |
| 7,646,953 B2 * | 1/2010 | Dowd et al. | 385/109 |
| 7,661,776 B2 | 2/2010 | Kangas | |
| 7,773,841 B2 * | 8/2010 | Varadarajan et al. | 385/32 |
| 7,946,350 B2 * | 5/2011 | Greenaway | 166/385 |
| 8,090,227 B2 | 1/2012 | Skinner | |
| 8,369,667 B2 * | 2/2013 | Rose | 385/102 |
| 2009/0266562 A1 * | 10/2009 | Greenaway | 166/385 |
| 2011/0240314 A1 * | 10/2011 | Greenaway | 166/385 |

OTHER PUBLICATIONS

"Fiber Optic Sensors-playing both sides of the equation" by Sanders, Jan. 2011 www.osa-opn.org.*
U.S. Appl. No. 13/359,159, John L. Maida et. al., Fiber Optic Line Purge System and Apparatus, filed Jan. 26, 2012, 26 pages.

* cited by examiner

*Primary Examiner* — Ryan Lepisto
*Assistant Examiner* — Guy Anderson
(74) *Attorney, Agent, or Firm* — Michael A. Ervin; Krueger Iselin LLP

(57) ABSTRACT

A system and method for controlling hydrogen concentration in optical sensing systems in subsurface wells. In an exemplary system the downhole optical fiber sensors are positioned within nested conduits and a controlled concentration hydrogen gas is flowed in a first direction through the first conduit, and flowed in a second direction through the annulus, wherein the second direction is opposite to the first direction.

28 Claims, 14 Drawing Sheets

FIBER OPTIC SENSING SYSTEM WITH HYDROGEN FLUSH

CROSS-REFERENCE TO RELATED APPLICATIONS

Not applicable.

BACKGROUND

The increasing use of fiber optic sensing systems in subterranean wells has been accompanied by the recognition that fiber optic systems can be affected over time by the harsh, hostile environment of subterranean wells. For example the combination of high temperatures and the presence of hydrogen. Hydrogen interacts with optical fibers leading to a phenomenon called hydrogen darkening that can quickly change the performance of the fiber. In extreme cases the fiber can become unusable with days after installation.

Optical fibers are often installed inside of conduits for protection and the conduit is installed in a down-hole wellbore. But even with conduits hydrogen incursion is highly likely.

Proposed solutions in the prior art have either attempted to increase the isolation of the fiber by improved barrier systems that protect the fiber or by the use of purging system that sweep the conduit with gases other than hydrogen.

There is a growing need for the improved systems for dealing with the hydrogen issue in fiber optic systems.

DETAILED DESCRIPTION

In the following detailed description, reference is made that illustrate embodiments of the present disclosure. These embodiments are described in sufficient detail to enable a person of ordinary skill in the art to practice these embodiments without undue experimentation. It should be understood, however, that the embodiments and examples described herein are given by way of illustration only, and not by way of limitation. Various substitutions, modifications, additions, and rearrangements may be made that remain potential applications of the disclosed techniques. Therefore, the description that follows is not to be taken as limiting on the scope of the appended claims.

The need described earlier can be met by a fiber optic sensing system, an optical fiber deployed in a conduit where the conduit is located in a down-hole well bore, and a delivery system capable of flushing the optical fiber with a gas with known concentrations of hydrogen.

One of the principles invoked in this disclosure is the use of an optical fiber with known responses to hydrogen exposure. An increasing number of optical fiber variants have been developed that have a known response to hydrogen exposure. This "known response" has the form of a known optical attenuation per unit length vs. wavelength, and known down-hole wellbore length so that the total optical attenuation is known. In addition the fiber optic sensing system has a known optical dynamic range at the operating wavelength.

The responses of different fiber optic sensor systems to hydrogen are complex, but known. For example Fiber Bragg Grating (FBG) systems and Brillouin based systems tend to have different responses to hydrogen than fiber-based systems such as Distributed Temperature Systems (DTS). But both have challenges that can be met by the control of hydrogen exposure.

For DTS systems total attenuation must be below a certain value, i.e. the dynamic range of the system. Fibers will have some attenuation that will vary with hydrogen concentration and wavelength. In addition wavelength dependent attenuation must be mitigated, and this is commonly done with double ended, or dual wavelength systems, or by flushing away all the hydrogen with, for example inert gases. Flushing with a known concentration of hydrogen will allow you to control both of these to some degree, and the rest can be taken care of with double ended or dual wavelength DTS systems.

Similarly, FBG based and Brillouin based systems will also have challenges that are different but can met by control of the hydrogen concentration as described in this disclosure. In FBG and Brillouin based systems total attenuation must be below a certain value, i.e. the dynamic range of the system, and the attenuation is wavelength dependent. The impact of the varying refractive index due to hydrogen must be mitigated.

Figure 1:
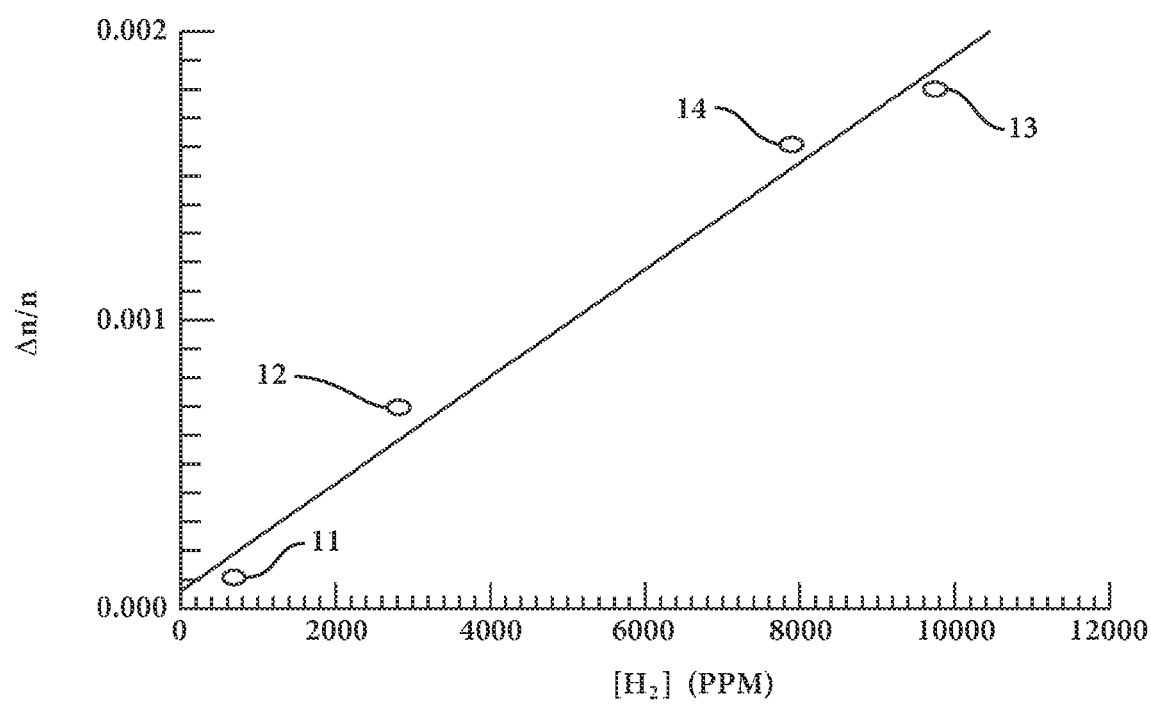
FIG. 1 is a graphical representation of data showing refractive index change as a function of hydrogen concentration.

FIG. 1 is a clear example of a response in a FBG or Brillouin based system. The data shown is a plot of refractive index change in such a system with varying levels of hydrogen environment ($H_2$ measured in parts per million). This is critical because in both FBG and Brillouin systems wavelength shifts are a function of refractive index. Both FBG based and Brillouin based systems can react in this manner and as a result a known concentration will allow a repeatable correction factor to be used.

The need described earlier can be met by a fiber optic sensing system, an optical fiber deployed in a conduit where the conduit is located in a down-hole well bore, and a delivery system capable of injecting a gas with controlled concentrations of hydrogen. More specifically the need can be met when the hydrogen concentration is known, the optical fiber has a known response to hydrogen exposure, i.e. optical attenuation per unit length vs. wavelength is known, the down-hole wellbore length is well known so the total optical attenuation is known, the fiber optic sensing system has a known optical dynamic range at the operating wavelength.

Provision of a controlled exposure of hydrogen to downhole fiber optic sensing systems can benefit single wavelength, dual-wavelength or multi-wavelength DTS systems and any single or multi-point single point sensing systems. These can be based on Raman and/or Rayleigh and/or Brillouin scattering, and the single or multi-point sensing system may be FBG based and/or Fabry-Perot based and/or based on other sensing principles well known to a person skilled in the art.

Figure 2:
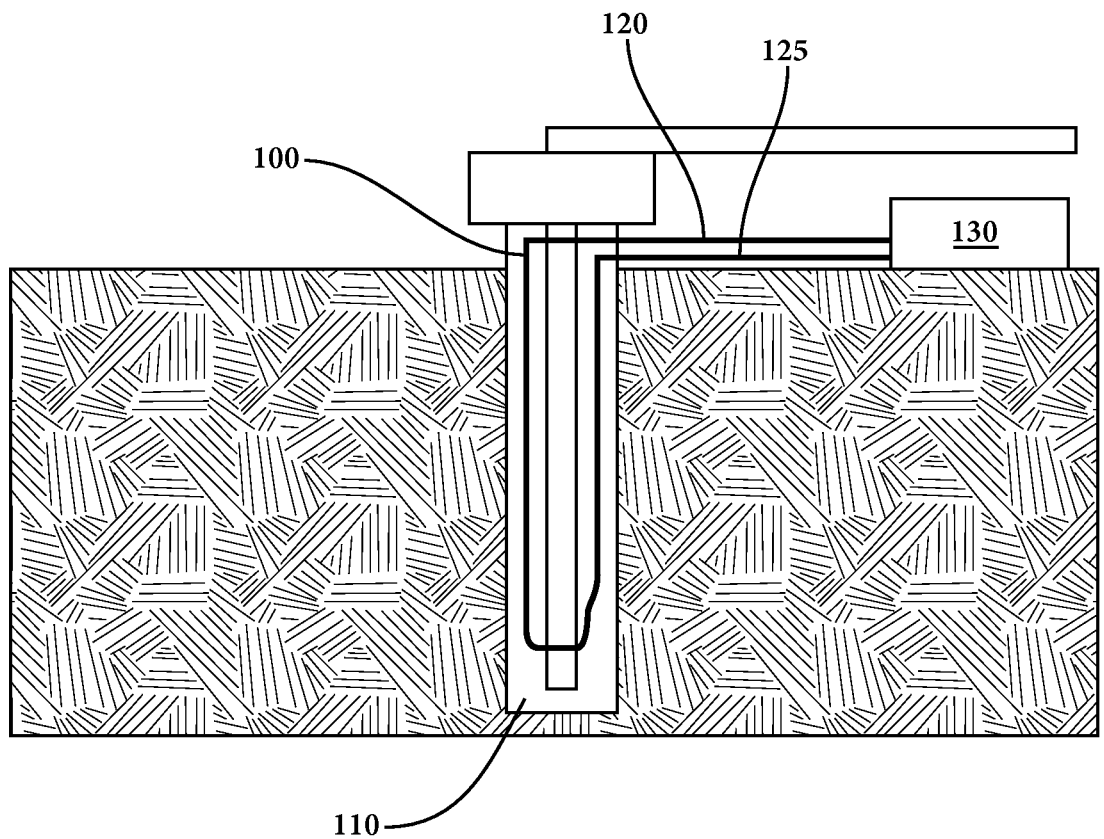
FIG. 2 illustrates one example of a conduit or a fiber optic deployed completely through the wellbore and back to the surface

Referring now to FIG. 2, one example configuration of fiber optic conduits in a wellbore 110 is shown. The fiber optic conduit 100 is shown deployed completely through the wellbore to the toe (bottom) and back to the surface by being connected at the toe via a 180-degree turnaround. Various effective designs of such 180-degree turnarounds are known—one example type is discussed later in this disclosure in FIG. 9. In the configuration of FIG. 2 both ends 120, 125 of the fiber optic conduit is connected at the surface to a control station 130. The fiber optic line (or lines) may be deployed within the conduits in multiple ways. In one embodiment the fiber optic line can be deployed into the conduit by pumping a single ended fiber optic line through the conduits using a pump fluid such as, for example, isopropanol, and the pump fluid carries the fiber optic line through the 180 degree turnaround and back to the surface, where it can be connected as a double ended system. The isopropanol can be easily removed later by flushing with a gas stream.

In another embodiment using the FIG. 2 configuration a single ended fiber can be installed that ends at the toe of the well. In that type of deployment a different type of turnaround might be used at the toe that is designed to capture the fiber at the toe while allowing the pump fluid to circulate. An example of this type of turnaround is discussed in FIG. 8.

Figure 3:
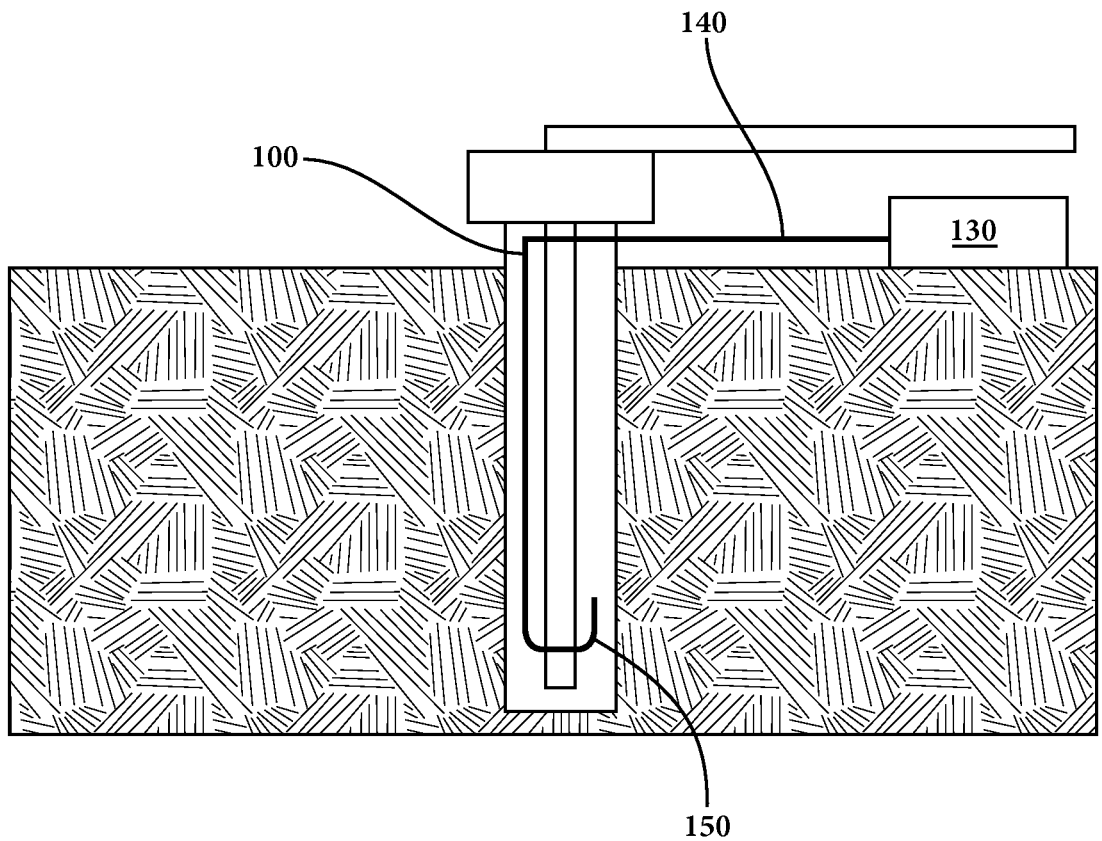
FIG. 3 illustrates an example of a conduit or fiber optic deployed in a J-tube arrangement.

In an alternative embodiment configuration, shown in FIG. 3, the fiber optic conduit 100 may be present in wellbore 110 in a J-tube installation. In this configuration, the surface end 140 of fiber optic conduit 100 is present at the surface of well bore 110 and connected to control station 130. In this embodiment the fiber optic conduit end 150 is located in the wellbore. A J-tube installation may be similar to the U-tube installation described above. However, in a J-tube installation, both ends of fiber optic conduit are not connected to control station 130. As a result, the carrier fluid may either be pumped into fiber optic line 100 at surface end 140 and then removed again from that end, or it may be pumped into fiber optic line 100 at end 140 and then allowed to exit at well end 150. Typically well end 150 may contain one or more one-way valves in series to prevent wellbore materials from entering fiber optic conduit 100. Fluid will exit the one or more one-way valves when the pressure in fiber optic line 100 exceeds a certain pressure at which the valves are designed to open. An example of that type of turnaround at the well toe is shown and discussed in FIG. 7.

Figure 7:
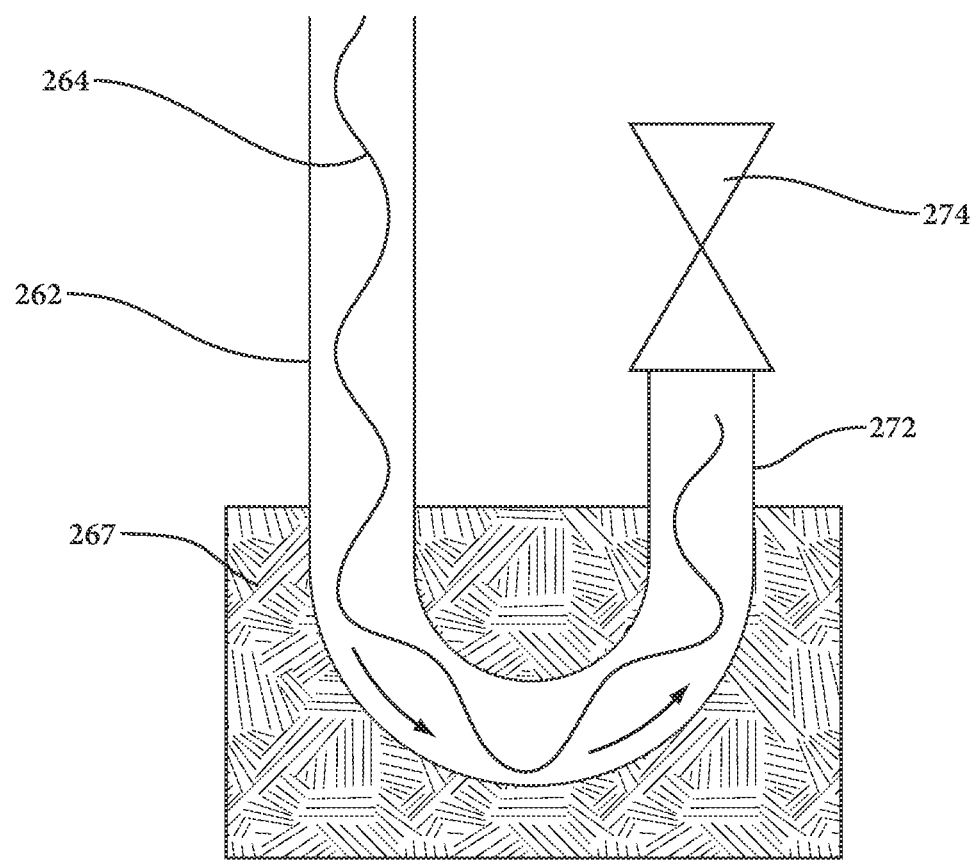
FIG. 7 illustrates an embodiment of a turn-around sub.

The 180-degree turn-around subs (TAS's) useful for various configurations can be of different designs depending on the needs and the sensing system to be employed. Some examples (not exhaustive) can be illustrated in FIGS. 7, 8, and 9. In each of these conduit tubes, for example ¼ inch diameter conduits 262 pass down the well bore and are connected near the toe to a turn-around sub. FIG. 7 illustrates a turn-around sub in which the channel 266 allows the delivery fluid (eg, isopropanol) to carry the fluid and fiber completely through the sub, and leave the fiber 264 in a J-type configuration. In these examples the exit side of the sub 272 may contain one or more one-way valves 274 in series to prevent wellbore materials from entering the fiber conduit line, as discussed previously in the J-configuration of FIG. 3. Fluid will exit the one or more one-way valves when the pressure in conduit 272 exceeds a certain pressure at which the valves are designed to open. In an alternative configuration (not shown) the conduit 272 could be deployed all the way back to the surface (without valve 274) even if the fiber is only deployed in a J-type configuration.

Figure 8:
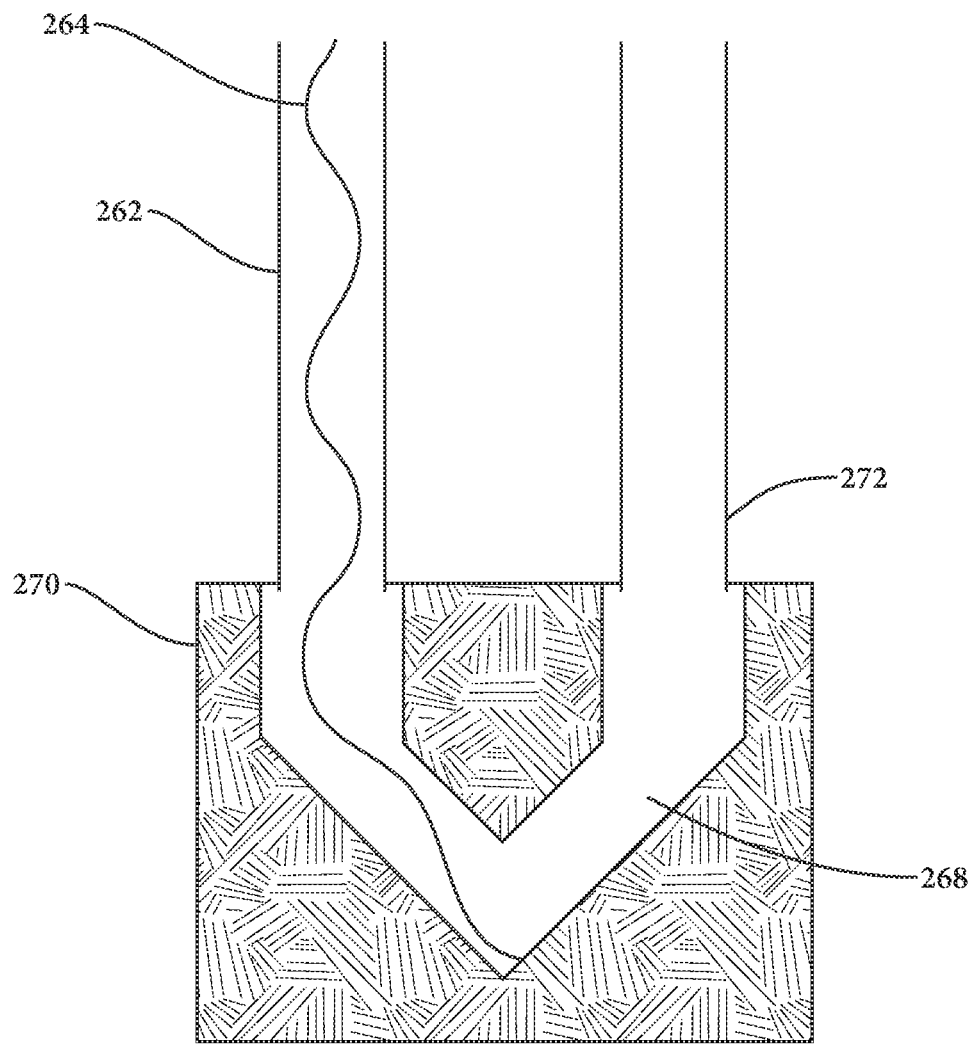
FIG. 8 illustrates another embodiment of a turn-around sub.
Figure 9:
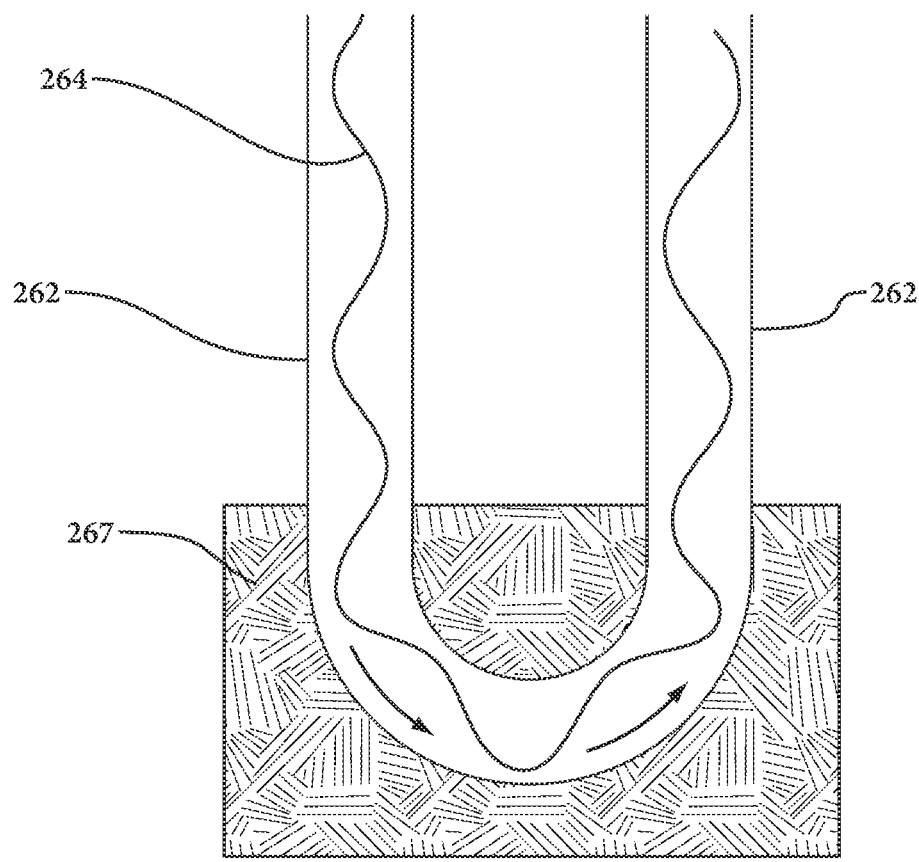
FIG. 9 illustrates another embodiment of a turn-around sub.

FIG. 8 illustrates another embodiment of a turnaround that is also designed to capture the fiber 264 as it is carried into the sub by the carrier fluid. The tight radius of the sub as well as the sharp v-shaped design at the base captures it. In this example the exit conduit 272 from the sub extends back to the surface and the carrier fluid is in a circulatory mode as described in the conduit configuration of FIG. 2. This mode of operation can be used for example when a single ended fiber is being deployed only down to the toe of the well. Alternately, when it is desired to pump an optical fiber 264 completely down a conduit 262 and back to the surface a configuration such as shown in FIG. 9 can be used. The bend radius of the sub is sized to allow the fiber to continue to easily flow with the deployment fluid back to the surface.

Figure 10:
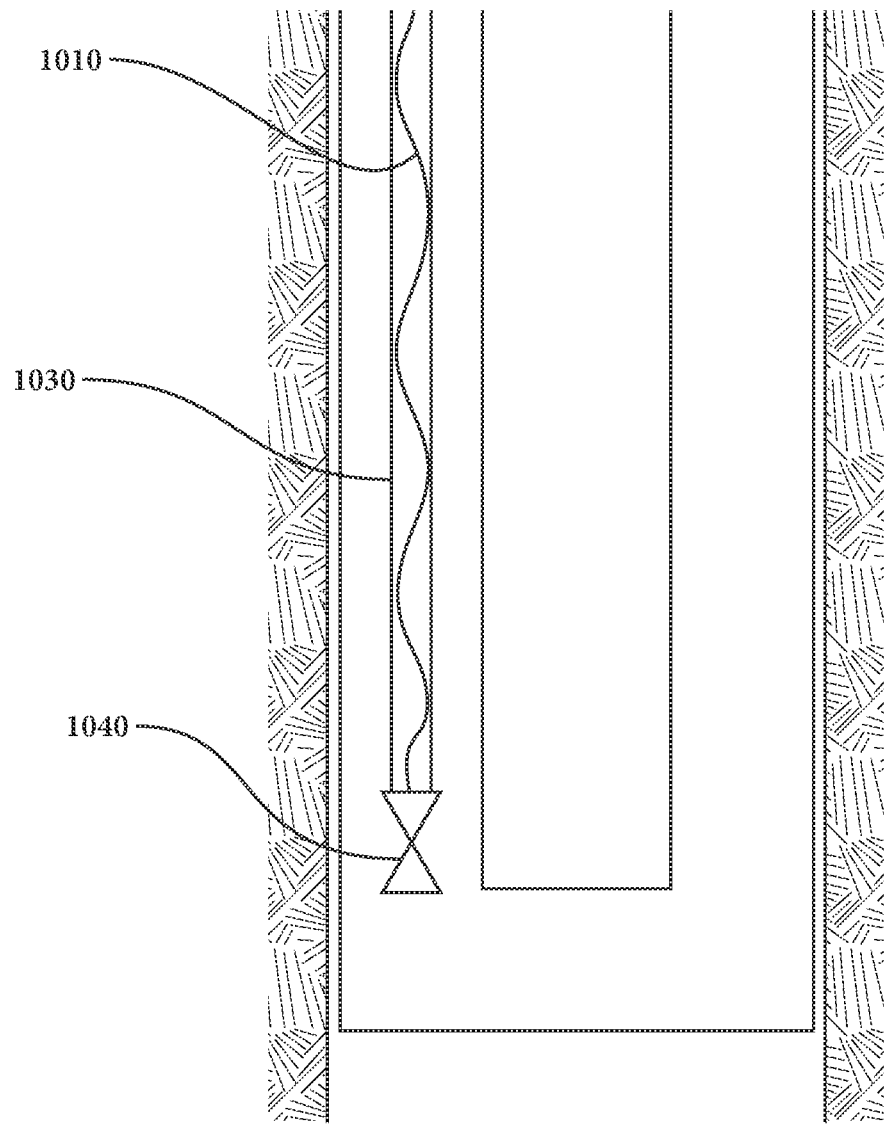
FIG. 10 illustrates an alternated method of deploying a fiber optic line down a conduit.

In another embodiment, shown in FIG. 10, a fiber optic 1010 can be deployed to the toe of a well by having a conduit 1030 that goes to the toe with one or more one-way valves 1040 in series at the end of the conduit. A delivery fluid (eg, isopropanol) can be used to carry fiber 1010 down to the toe and exit valve 1040 can be used to stop the fiber. The carrier fluid flow can then be stopped when the delivery pressure drops below a prescribed value. The carrier fluid can then be purged out with an inert gas.

Figure 4:
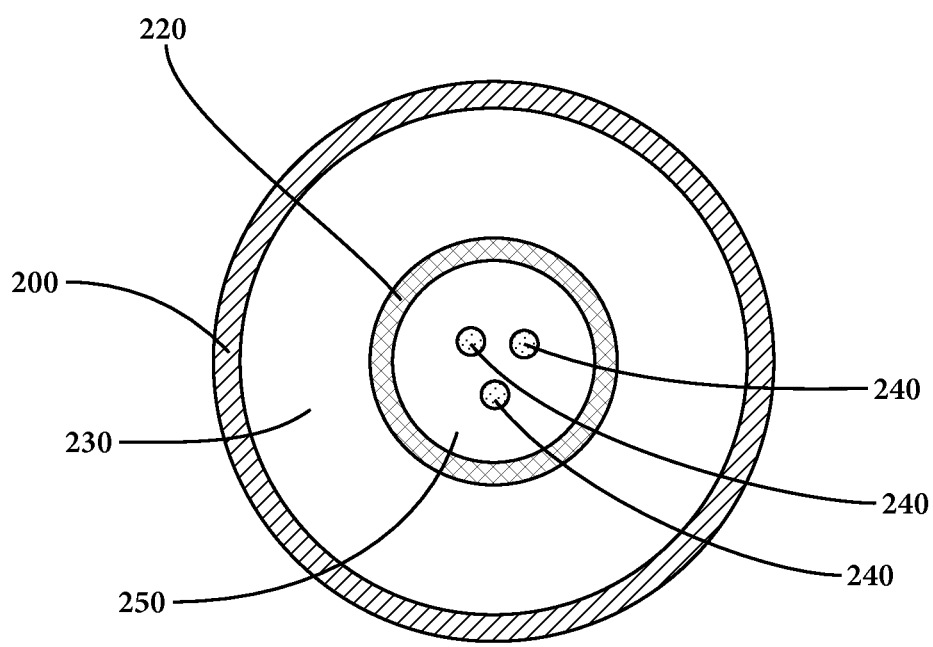
FIG. 4 illustrates an example cross section of a co-axial fiber optic line that may be used in conjunction with certain embodiments of the present disclosure.
Figure 5:
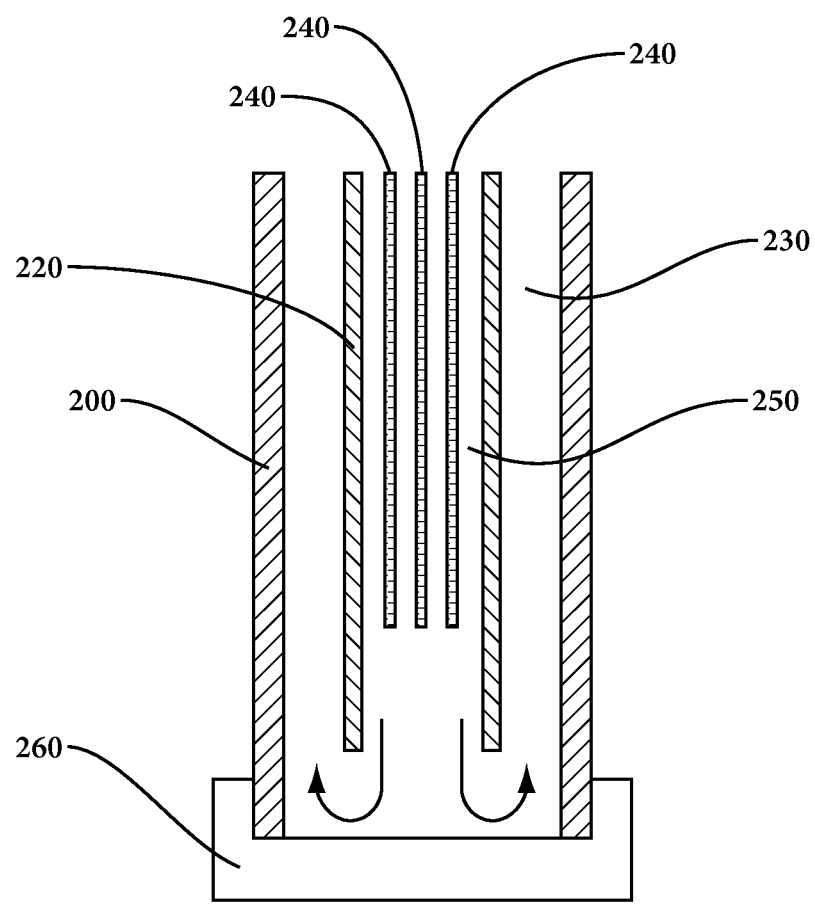
FIG. 5 illustrates a possible gas flow in a fiber optic line of FIG. 4.
Figure 6:
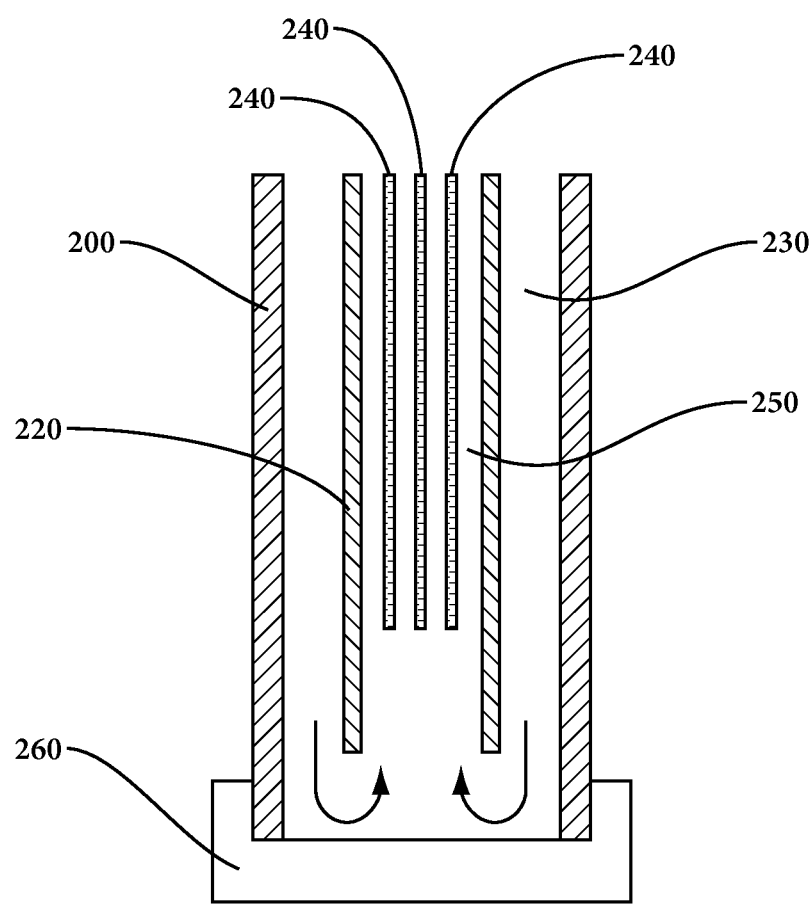
FIG. 6 illustrates an alternate gas flow in a fiber optic line of FIG. 4.

Other configurations of fiber optic lines in wellbores are possible. One such possibility is shown in FIGS. 4, 5, and 6, which represent variations of Fibers in Metal Tube (FIMT). In these configurations the fiber optic line may be a co-axial fiber optic line including outer tube 200, and inner tube 220, which may also be metallic or another non-corrodible and durable material, and end cap 260. Optical fibers 240 are located inside of inner tube 220. Inner volume 230 is located between outer tube 200 and inner tube 220. Inner volume 250 is located within inner tube 220. The optical fibers 240 could be part of a DTS sensor system, could be a Fiber Bragg Gratings system, or part of a Brillouin based system.

In addition to the configuration of FIG. 4, more complex configurations involving coiled tubing configurations can be envisioned and could be very useful. In one embodiment the outer tube 200 could be for example a coiled tube of 1.25 in. diameter and include not one but multiple 0.25 in. inner tubes 220 (not shown). In one embodiment two of the 220 tubes could be tied together with a 180 turnaround sub at the toe of the well as part of a double ended DTS system, one of the 220 tubes could only have a single fiber with a sensor at the end, for example an extrinsic Fabry-Perot pressure sensor with an FBG for temperature sensing. And in the case of a pressure sensor it would have to have a port coupled to the outside of the 1.25 in coiled tube. One of the 220 tubes could be empty. Other combinations of the multiple 220 tubes are possible, including a tube dedicated to carrying a hydrogen flush gas flow. All of these are design choices and are anticipated in this disclosure.

In all of the various configurations discussed herein, all of which may be employed at different times in downhole environments for placing and using either distributed fiber optic sensing systems such as DTS or DAS sensors or single or multiple placed fiber optic based sensors, the use of a system for flushing the fiber optic sensing systems with a known and controlled hydrogen concentration will be described and used.

As illustrated in FIG. 5, which corresponds to the configuration of FIG. 4, in one embodiment a hydrogen gas concentration flush gas stream may flow down inner volume 250 until it reaches end cap 260, at which point it may flow up inner volume 230 to exit the fiber optic line from the same end at which it entered. Alternatively, as illustrated in FIG. 6 fluid may flow down inner volume 230 until it reaches end cap 260 at which point it may flow up inner volume 250 to exit the fiber optic line from the same end at which it entered.

The configurations discussed above can be employed in a variety of downhole applications in which it is desired to control the hydrogen exposure of fiber optic sensors. These can include DTS systems based on Raman and/or Rayleigh and/or Brillouin scattering, and the single or multi-point sensing system may be FBG based and/or Fabry-Perot based and/or based on other sensing principles well known to a person skilled in the art.

Figure 11:
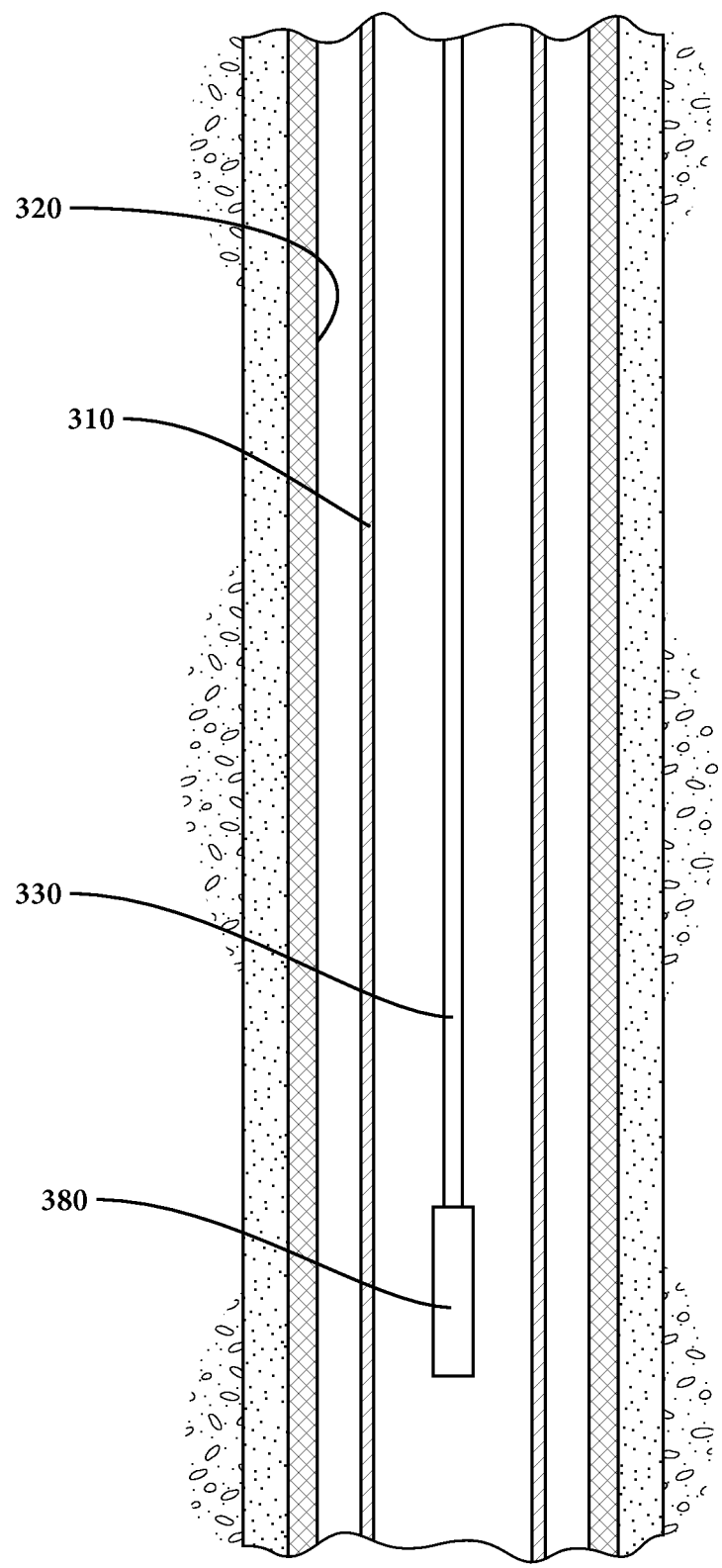
FIG. 11 is a cross-sectional view of a deployment of a production string in a wellbore embodying principles of this disclosure.
Figure 12:
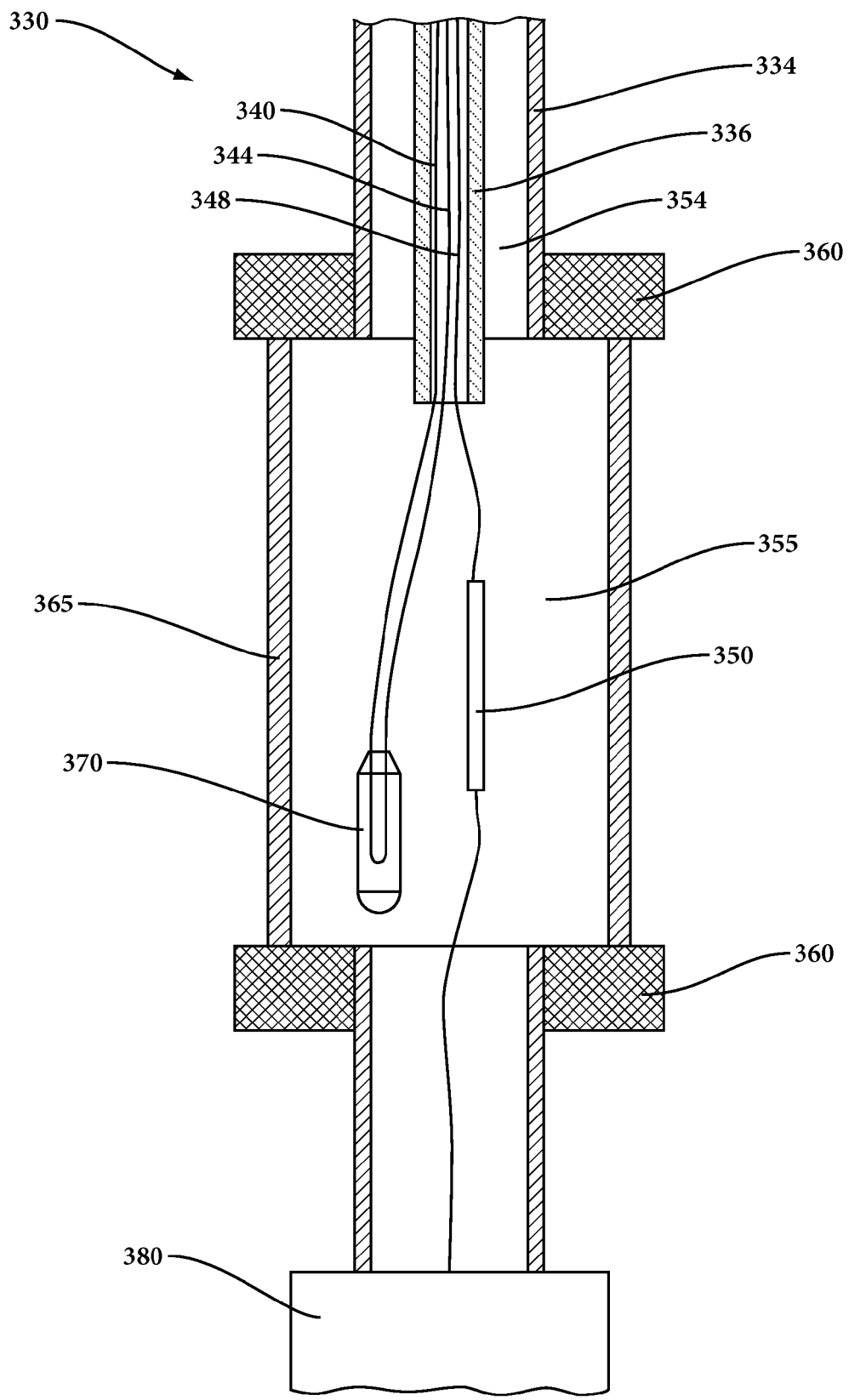
FIG. 12 is an enlarged scale schematic cross-section view of an optical sensing system of this disclosure.

Other examples of sensor deployments in a downhole wellbore can be illustrated in FIGS. 11 and 12. In FIG. 11 production tubing string 310 has been installed in a wellbore 320. Attached to the tubing string 310 during installation is a conduit assembly 330 and a sensor 380. The conduit assembly 330 and sensor 380 may be separately attached to the tubing string 310 (for example, using clamps, etc.), or the conduit assembly and/or the sensor 380 could be integrally formed with the tubing string 310.

As another alternative, the conduit assembly 330 and/or sensor 380 could be installed in the wellbore 320 whether or not the tubing string 310 is also installed in the wellbore. Therefore, it should be clearly understood that the principles of the disclosure herein are not limited in any way to the details of the system illustrated in the exemplary drawings or as described herein.

Referring additionally now to FIG. 12, an enlarged scale cross-sectional view of a portion of the system shown in FIG. 11 is representatively illustrated. In this enlarged view it may be seen that the conduit assembly 330 includes an inner conduit 336 and an outer conduit 334.

Multiple optical waveguides or lines 340, 344, 348 are contained within the inner conduit 336. Although three lines are depicted in FIG. 12, any number of optical lines (including one) may be used. The lines 340, 344, 348 may be of the type known as optical fibers or any other type of optical waveguide.

In addition, any number of conduits may be used. Although the conduit 336 is described for convenience herein as an "inner" conduit, another conduit could be contained within the conduit 336, and although the conduit 334 is described for convenience herein as an "outer" conduit, another conduit could be external to the conduit 334. The conduits may be made of any suitable material, such as stainless steel, polymers, composites, etc.

The optical lines 340,344 could be used for distributed temperature sensing (DTS), a technique well known to those skilled in the art, in which backscattered light is analyzed to determine the temperature distribution along optical lines or fibers. In this manner, the lines 340,344 themselves comprise temperature sensors in the optical sensing system.

The optical line 348 is preferably operatively connected to the sensor 380 (for example, via a fusion splice 350). The sensor 380 could be a sensor designed to detect a property at a single location, such as a pressure sensor. The sensor 380 could be an optical sensor, or it could be another type of sensor, either single or multi-point sensing system and may be FBG based and/or Fabry-Perot based and/or based on other sensing principles well known to a person skilled in the art.

The splice 350 is preferably contained within a chamber 355. The chamber 355 is preferably connected between the sensor 380 and a lower end of the conduit assembly, for example, using pressure isolating fittings 360 at either end of a tubular housing 365. However, other arrangements and configurations may be used in keeping with the principles of the disclosure.

In the example of FIG. 12, a conventional 180-degree turnaround 370 in chamber 355 is operatively connected to the lines 340, 344, so that the lines and the turnaround form a continuous optical waveguide from a remote location (such as the earth's surface) to a downhole location, and back to the remote location. This arrangement permits more accurate double-ended (as opposed to single-ended) distributed temperature measurements to be obtained using the lines 340, 344.

As shown in FIG. 12, the chamber 355 is in communication with the interior of the inner conduit 336, and in communication with the annulus 354 between the conduits 334 and 336. In this manner, a continuous flow passage is formed from the remote location (such as the earth's surface, sea floor, etc.) to the downhole location at the chamber 355, and back to the remote location. This configuration permits a controlled concentration hydrogen medium to be flowed in one direction downhole, and flow in an opposite direction uphole, in order to create a controlled hydrogen concentration environment around optical lines 340, 344, and 348.

Figure 13:
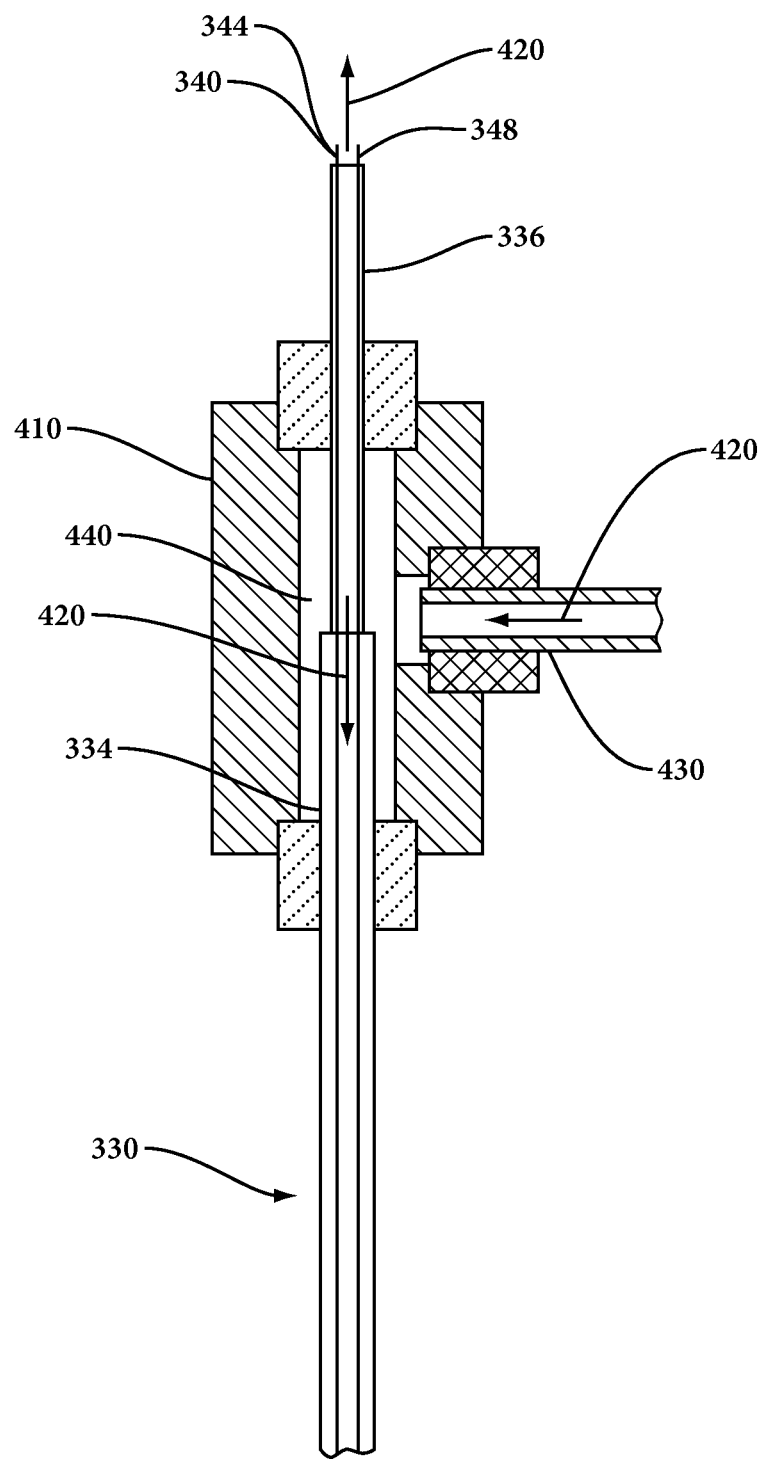
FIG. 13 exhibits one example approach for delivering a controlled concentration of hydrogen gas to the optical sensing system.

Two exemplary approaches can be shown for introducing the hydrogen flow. Referring first to FIG. 13, as well as FIG. 12, one method for controlling the hydrogen concentration around the lines 340, 344, and 348 in the conduit assembly 330 is illustrated. This method utilizes a flow control device 410 connected to an upper end of the conduit assembly 330 at the remote location.

The controlled concentration hydrogen gas 420 is flowed via a conduit 430 into an interior chamber 440 of device 410. The chamber 440 is in communication with the annulus 354 between the conduits 334, 336. Thus, the controlled concentration hydrogen gas 420 flows downhole through the annulus 354 between the conduits 334, 336, into the chamber 355 at the lower end of the conduit assembly 330, and then back uphole to the remote location via the interior of the inner conduit 336. In this manner, the hydrogen concentration surrounding the lines 340, 344, and 348 in the conduit assembly 330 is maintained in a controlled state.

Figure 14:
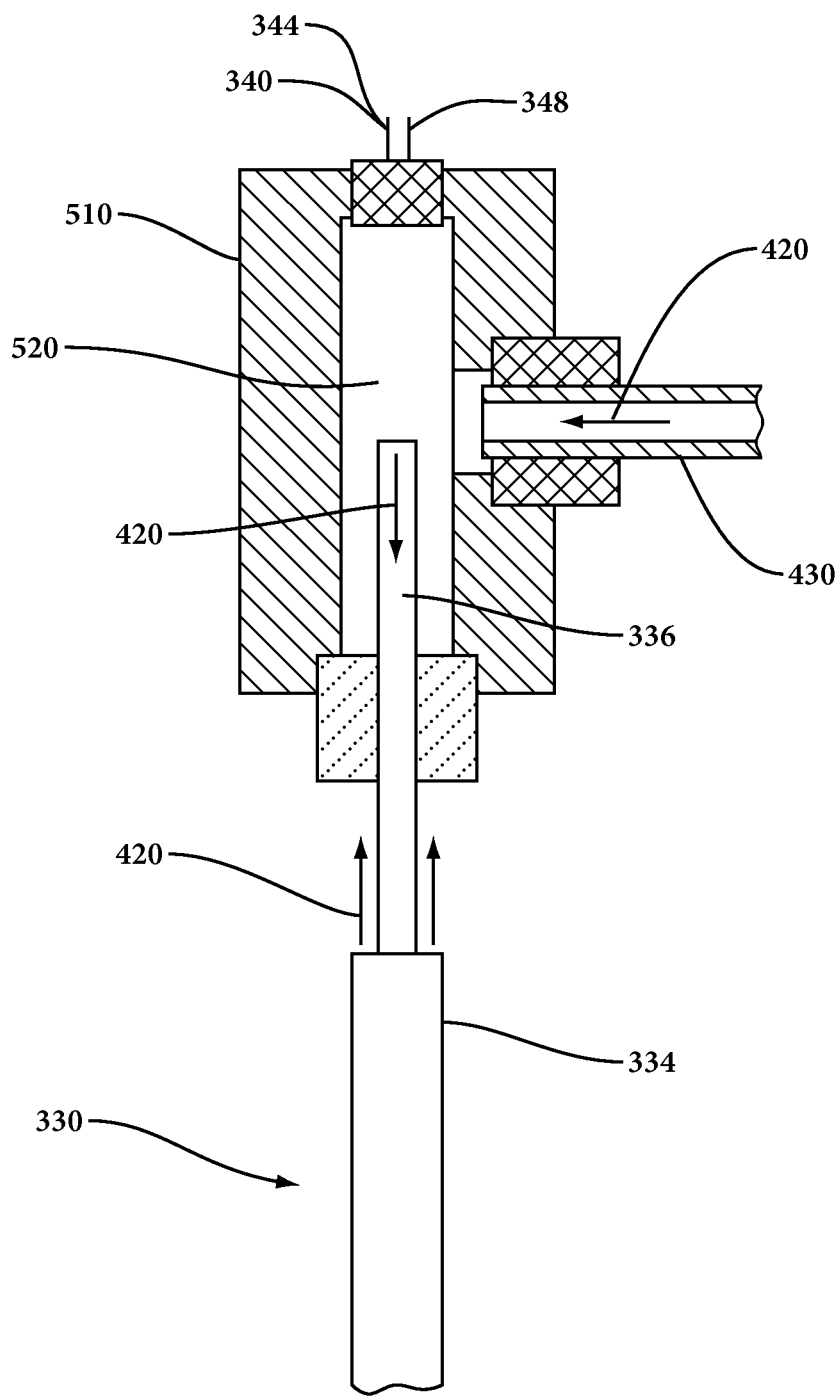
FIG. 14 exhibits an alternate approach for delivering a controlled concentration of hydrogen gas to the optical sensing system.

An alternate approach for controlling a hydrogen gas flow into the conduit assembly 330 and surrounding the optical lines 340, 344, and 348 is exhibited in FIG. 14 (with references to FIG. 12). This method utilizes a somewhat differently configured flow device 510 connected to an upper end of the conduit assembly 330 at the remote location.

The controlled concentration hydrogen gas 420 is flowed via the conduit 430 into an interior chamber 520 of the device 510. The chamber 520 is in communication with the interior of the conduit 336. Thus, the controlled concentration hydrogen gas 420 flows downhole through the interior of the inner conduit 336, into the chamber 355 at the lower end of the conduit assembly 330, and then back uphole to the remote location via the annulus 354 between the conduits 334, 336. In this manner, the hydrogen concentration surrounding the lines 340, 344, and 348 in the conduit assembly 330 is maintained in a controlled state.

Although not shown, the flow of a controlled concentration hydrogen gas 420 into conduit 430 could be done with a number of art-recognized methods. For example at the upper end of the conduit assembly 330 at the remote location a pre-prepared pressure bottle containing a controlled concentration hydrogen gas with appropriate art-recognized regulators could be used to periodically flush a known volume of the gas throughout conduit assembly 330.

The flow patterns of the hydrogen flush gas described in relation to FIGS. 4-6 and in FIGS. 11-12 might be different for the other configurations mentioned herein. For example in the conduit configuration of FIG. 2, in which a fiber optic conduit 100 is shown deployed completely through the wellbore to the toe (bottom) and back to the surface by being connected at the toe via a 180-degree turnaround. In that configuration the hydrogen flush gas could be simply slowly flowed from the surface down the conduit, and through the turnaround and back to the surface, either once through or in a circulatory fashion.

In the configuration of FIG. 3 hydrogen flush would be supplied by periodic purges of the hydrogen flush gas down the conduit and out the turnaround on the exit side. In that configuration the turnaround might be like the one in FIG. 8. The exit side of the sub 272 may contain one or more one-way valves 274 in series to prevent wellbore materials from entering the fiber optic line. The gas flow will exit the one or more one-way valves when the pressure of the hydrogen flush gas in the conduit 262, 272 exceeds a certain pressure at which the valves are designed to open.

In a similar manner the configuration of FIG. 10, in which an optical fiber is deployed to the toe of a well, the hydrogen flush would be supplied by periodic purges of the hydrogen flush gas down the conduit and out exit valve 1040. The gas flow will exit valve 1040 when the pressure of the hydrogen flush gas in the conduit 1030 exceeds a certain pressure at which the valve is designed to open.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

What is claimed is:

1. A system for controlling hydrogen concentration in optical sensing systems in subsurface wells, comprising:
   a. at least one optical fiber line;
   b. at least one tubular conduit, the at least one optical fiber line being positioned within the at least one tubular conduit;
   c. a hydrogen gas system for flowing a hydrogen flush gas of known concentration from the surface side of the subsurface well into the subsurface well through the at least one tubular conduit;
   d. wherein the at least one optical fiber line has a known optical attenuation per unit length vs. wavelength, and a known downhole total optical attenuation;
   e. wherein the at least one tubular conduit is positioned from the surface side of the subsurface well in a first direction to a prescribed subsurface distance and then is reversed through a 180 degree turnaround into an opposite direction and returned the surface;
   f. wherein the at least one optical fiber line is single ended and deployed only to the 180 turnaround; and
   g. wherein the controlled concentration hydrogen gas is flowed downhole in the at least one tubular conduit and returns to the surface.

2. The system for controlling hydrogen concentration in optical sensing systems in subsurface wells of claim 1 wherein the at least one optical fiber line is operatively connected to a downhole sensor.

3. The system for controlling hydrogen concentration in optical sensing systems in subsurface wells of claim 2 wherein the downhole sensor is Raman based.

4. The system for controlling hydrogen concentration in optical sensing systems in subsurface wells of claim 2 wherein the downhole sensor is FBG based.

5. The system for controlling hydrogen concentration in optical sensing systems in subsurface wells of claim 2 wherein the downhole sensor is Brillouin based.

6. The system for controlling hydrogen concentration in optical sensing systems in subsurface wells of claim 2 wherein the downhole sensor is a Fabry-Perot pressure based sensor.

7. The system for controlling hydrogen concentration in downhole optical sensing systems in subsurface wells of claim 1 wherein the at least one optical fiber line is single ended and is positioned only to the 180 degree turnaround into a J-type configuration and not back to the surface.

8. The system for controlling hydrogen concentration in downhole optical sensing systems in subsurface wells of claim 1 wherein the at least one tubular conduit is deployed from the surface side of the subsurface well to a prescribed subsurface distance and has at least one one-way exit valve to allow flow out of the tubular conduit when the tubular conduit is above a prescribed pressure.

9. The system for controlling hydrogen concentration in downhole optical sensing systems in subsurface wells of claim 1 wherein the at least one tubular conduit, with the at least one optical fiber line being positioned within the at least one tubular conduit is positioned within a larger coiled tube containing multiple tubular conduits and the hydrogen gas system periodically flows a known concentration of hydrogen containing gas from the surface side of the subsurface well through the far end of the coiled tube and out of a one-way exit valve.

10. The system for controlling hydrogen concentration in downhole optical sensing systems in subsurface wells of claim 9 wherein at least two of the tubular conduits extend from the surface to a prescribed distance in the subsurface well and are tied together with a 180 degree turnaround.

11. The system for controlling hydrogen concentration in downhole optical sensing systems in subsurface wells of claim 1 wherein the at least one tubular conduits comprise at least first and second tubular conduits, the first tubular conduit being positioned within the second tubular conduit, and the at least one optical fiber line being positioned within at least one of the first and second tubular conduits, an interior of the first tubular conduit being in fluid communication with an annulus between the first and second tubular conduits, and the interior of the first tubular conduit and the annulus being isolated from well fluids when the optical sensing system is positioned downhole.

12. The system for controlling hydrogen concentration in downhole optical sensing systems in subsurface wells of claim 11 wherein the optical fiber line is positioned within the first tubular conduit.

13. The system for controlling hydrogen concentration in downhole optical sensing systems in subsurface wells of claim 11 wherein the controlled concentration hydrogen gas is flowed downhole in the first tubular conduit and returns in the annulus.

14. The system for controlling hydrogen concentration in downhole optical sensing systems in subsurface wells of claim 11 wherein the controlled concentration hydrogen gas is flowed downhole in the annulus and returns in the first tubular conduit.

15. The system for controlling hydrogen concentration in downhole optical sensing systems in subsurface wells of claim 1 further comprising a downhole chamber in fluid communication with the interior of the first conduit and the annulus.

16. The system for controlling hydrogen concentration in downhole optical sensing systems in subsurface wells of claim 15 further comprising a 180-degree turnaround in the optical fiber line within the downhole chamber.

17. A method for controlling hydrogen concentration in downhole optical sensing systems in subsurface wells, the method comprising:
   a. positioning at least one tubular conduit from a surface installation to a proscribed distance into a wellbore;
   b. positioning at least one optical fiber line in the at least one tubular conduit;
   c. flowing a controlled concentration hydrogen from the surface side of the subsurface well into the subsurface well through the at least one tubular conduit;
   d. wherein the at least one optical fiber line has a known optical attenuation per unit length vs. wavelength, and a known downhole total optical attenuation;
   e. wherein the at least one tubular conduit is positioned from the surface side of the subsurface well in a first direction to a prescribed subsurface distance and then is reversed through a 180 degree turnaround into an opposite direction and returned the surface;
   f. wherein the at least one optical fiber line is single ended and deployed only to the 180 turnaround; and
   g. wherein the controlled concentration hydrogen gas is flowed downhole in the at least one tubular conduit and returns to the surface.

18. The method for controlling hydrogen concentration in downhole optical sensing systems in subsurface wells of claim 17, wherein the flowing of a controlled concentration hydrogen from the surface side of the subsurface well into the subsurface well through the at least one tubular conduit is done periodically and the flow is vented through a one way valve at the exit of the tubular conduit.

19. The method for controlling hydrogen concentration in downhole optical sensing systems in subsurface wells of claim 17 wherein the at least one tubular conduit comprise at least first and second tubular conduits, the first tubular conduit being positioned within the second conduit, and the at least one optical fiber line being positioned within at least one of the first and second tubular conduits, an interior of the first tubular conduit being in fluid communication with an annulus between the first and second tubular conduits, and the interior of the first tubular conduit and the annulus being isolated from well fluids when the optical sensing system is positioned downhole.

20. The method for controlling hydrogen concentration in downhole optical sensing systems in subsurface wells of claim 19 wherein the flowing of a controlled concentration hydrogen gas further comprises flowing the controlled concentration hydrogen gas downhole in the first tubular conduit and returning the controlled concentration hydrogen gas from downhole in the annulus.

21. The method for controlling hydrogen concentration in downhole optical sensing systems in subsurface wells of claim 19 wherein the flowing of a controlled concentration hydrogen gas further comprises flowing the controlled concentration hydrogen gas downhole in the annulus and returning the controlled concentration hydrogen gas from downhole in the first tubular conduit.

22. A method for controlling hydrogen concentration in downhole optical sensing systems in subsurface wells, the method comprising:
   a. positioning at least one coiled tube from a surface installation to a proscribed distance into a wellbore;
   b. positioning at least one tubular conduit in the at least one coiled tube;
   c. positioning at least one optical fiber line in the at least one tubular conduit;
   d. periodically flowing a controlled concentration hydrogen gas from the surface installation through the at least one coiled tube and venting the flow through a one way exit valve at the exit of the coiled tubing.

23. The method for controlling hydrogen concentration in downhole optical sensing systems in subsurface wells of claim 22 wherein at least two of the at least one tubular conduits extend from the surface to a prescribed distance in the subsurface well and are tied together with a 180 degree turnaround.

24. The method for controlling hydrogen concentration in downhole optical sensing systems in subsurface wells of claim 17 wherein the at least one optical fiber line is operatively connected to a downhole sensor.

25. The method for controlling hydrogen concentration in downhole optical sensing systems in subsurface wells of claim 24 wherein the downhole sensor is Raman based.

26. The method for controlling hydrogen concentration in downhole optical sensing systems in subsurface wells of claim 24 wherein the downhole sensor is FBG based.

27. The method for controlling hydrogen concentration in downhole optical sensing systems in subsurface wells of claim 24 wherein the downhole sensor is Brillouin based.

28. The method for controlling hydrogen concentration in downhole optical sensing systems in subsurface wells of claim 24 wherein the downhole sensor is a Fabry-Perot pressure based sensor.

* * * * *